United States Patent
Nakade et al.

(10) Patent No.: US 7,052,718 B2
(45) Date of Patent: May 30, 2006

(54) METAL OXIDE-ORGANOPOLYSILOXANE HYBRID POWDER AND A METHOD FOR THE PREPARATION THEREOF AND A COSMETIC COMPOSITION THEREWITH

(75) Inventors: Masato Nakade, Kita-ku (JP); Koichi Kameyama, Kita-ku (JP)

(73) Assignee: Kose Corporation, Tokyo (JP)

( * ) Notice: Subject to any disclaimer, the term of this patent is extended or adjusted under 35 U.S.C. 154(b) by 340 days.

(21) Appl. No.: 10/078,402

(22) Filed: Feb. 21, 2002

(65) Prior Publication Data

US 2002/0172697 A1   Nov. 21, 2002

(30) Foreign Application Priority Data

Feb. 23, 2001   (JP) ............................ 2001-048172

(51) Int. Cl.
*A61K 9/14*   (2006.01)
*A61K 7/00*   (2006.01)

(52) U.S. Cl. ...................................... 424/489; 424/401
(58) Field of Classification Search ................ 424/401, 424/489, 70.9, 641; 524/413, 497
See application file for complete search history.

(56) References Cited

U.S. PATENT DOCUMENTS 5,843,525 A * 12/1998 Shibasaki et al. ............ 427/214
6,013,247 A *  1/2000 Bara et al. ..................... 424/59
6,200,580 B1 *  3/2001 Horino et al. ................ 424/401

FOREIGN PATENT DOCUMENTS

| JP | 07265686  | 10/1995 |
|----|-----------|---------|
| JP | 10095852  |  4/1998 |
| JP | 2001064395|  3/2001 |

OTHER PUBLICATIONS

B. Wang, et al., New Ti-PTMO and Zr-PTMO Ceramer Hybrid . . . ,Journal of Polymer Science, vol. 29, 1991, pp. 905-909.

* cited by examiner

Primary Examiner—Thurman K. Page
Assistant Examiner—Blessing Fubara
(74) Attorney, Agent, or Firm—Sherman & Associates

(57) ABSTRACT

The present invention is to provide a metal oxide.organopolysiloxane hybrid powder, wherein a silicon atom of organopolysiloxane is bonded by covalent bond with a metal atom through an oxygen atom and complicated homogeneously. Titanium and/or zirconium is desirably used as the above mentioned metal atom. Especially, a porous titanium oxide.organopolysiloxane hybrid powder whose specific surface area is larger than 50 $m^2/g$ is desirably used. Said hybrid powder can be produced by generating sol by hydrolysis of metal alkoxide, adding reactive organopolysiloxane to said sol to generate hybrid sol solution, then precipitating it. The method to produce titanium oxide.silica composite by the heat treatment of porous titanium oxide-.organopolysiloxane hybrid powder can be also mentioned. By making hybrid, the optical properties of metal oxide powder can be controlled and dispersing ability, dispersing stability, water repellency and hard feeling can be improved. By blending this hybrid powder in cosmetic composition, the cosmetic composition which is excellent at feeling at the actual use, natural makeup, long lasting and ultra violet ray screening effect can be obtained.

2 Claims, No Drawings

METAL OXIDE-ORGANOPOLYSILOXANE HYBRID POWDER AND A METHOD FOR THE PREPARATION THEREOF AND A COSMETIC COMPOSITION THEREWITH

BACKGROUND OF THE INVENTION

1. Field of the Invention

The present invention relates to metal oxide.organopolysiloxane hybrid particles, and a powder composition made from those particles, and a method for the preparation thereof, and still further relates to a cosmetic composition in which said metal oxide organopolysiloxane hybrid particles are blended.

2. Description of the Prior Art

The powder of titanium oxide, which is well-known to have high refractive index among metal oxides is broadly used as the white pigment, because of it's excellent hiding power and is chemically stabilized. However, this high refractive index sometimes can become a weak point. Especially, when it is applied in a cosmetic composition, it becomes a ground to cause unnatural makeup, which is so called as "an excessively pale-white look". Therefore, when a metal oxide having high refractive index e.g. titanium oxide is used in a cosmetic composition, various countermeasures to avoid said serious problem are taken, for example, altering the shape or particle size of the powder or forming a complex with other materials. However, since the refractive index is the essential feature of each powder, above mentioned countermeasures are not sufficient to dissolve said serious problem.

Further, some metal oxides have a tendency to cause cohesion in medium, and powder of these metal oxides are difficult to maintain stable dispersion state. Still further, since the powder of metal oxide is easily wetted by water, a coated film of blended product in which these mentioned powders are blended have a defect of weak resistance to water. For the purpose to dissolve these problems, the method to provide water repellency by treating the surface of powder with a surface treatment agent such as organopolysiloxane or fluorine type high molecular compound. However, although it is possible to provide water repellency and to improve water resistance by said method, the improvement of dispersing ability and dispersing stability are not sufficient.

In the meanwhile, porous inorganic powder represented by silica gel is widely used as an absorbing agent, as an impregnating agent or as a carrier of catalyst based on it's large specific surface area. And in the field of materials for cosmetic composition, the porous powder is used in various forms. Mainly, the porous inorganic powder is blended in a cosmetic compound for the purpose to obtain long-lasting of makeup by removing sebum or sweat, or to provide light and smooth feeling.

A hybrid material composed of metal oxide and organic compound have been developed and a powder of hybrid material prepared by covalent bond of metal oxide and organic high molecular compound is proposed (JP7-265686A). Typically, the powder of the proposed invention can be obtained by following method. A seed particle, which is high molecular compound, obtained by polymerizing vinyl type monomer, is swelled by a swelling solvent containing polymerable metal alkoxide possessing vinyl group. After that, said polymerable metal alkoxide is polymerized. Then, the hybrid of the present invention can be obtained by carrying out hydrolysis and condensation reaction. The proposed invention is characterized by particles having uniform particle size.

OBJECT OF THE INVENTION

The object of the present invention is to provide a metal oxide hybrid powder which can control the optical property of metal oxide such as refractive index and whose dispersing ability, dispersion stability and hard feeling are improved, further water repellency is provided maintaining a special feature of metal oxide. And other object of the present invention is to provide a cosmetic composition to which the metal oxide hybrid powder is blended.

Further, the other object of the present invention is to provide titanium oxide.organopolysiloxane hybrid powder having large specific surface area, which is a porous material, having optical and mechanical properties improved. And, the other object of the present invention is to provide a porous titanium oxide.silica hybrid practically using property of titanium oxide. Furthermore, the other object of the present invention is to provide a cosmetic composition to which titanium oxide.organopolysiloxane hybrid powder or porous titanium oxide.silica composite is blended.

BRIEF SUMMARY OF THE INVENTION

The present invention relates to a metal oxide.organopolysiloxane hybrid powder, wherein a silicon atom of organopolysiloxane is bonded by covalent bond with a metal atom through an oxygen atom, and relates to a producing method thereof. Further, the present invention relates to a cosmetic compound in which the metal oxide.organopolysiloxane hybrid powder is blended.

The present invention is further relating to a porous titanium oxide.organopolysiloxane hybrid powder, wherein a silicon atom of the organopolysiloxane is bonded by covalent bond with a titanium atom through an oxygen atom and hybridized homogeneously and whose specific surface area is larger than 50 $m^2/g$ and a producing method thereof. Furthermore, the present invention relates to a cosmetic composition in which the porous titanium oxide.organopolysiloxane hybrid powder is blended.

Still further, the present invention relates to a method to produce a porous titanium oxide.silica composite produced by heat treatment of above mentioned porous titanium oxide.organopolysiloxane hybrid powder, and relates to the porous titanium oxide.silica composite obtained by above mentioned method. Yet further, the present invention relates to a cosmetic composition in which the porous titanium oxide silica composite is blended.

DETAILED DESCRIPTION OF THE INVENTION

The metal oxide.organopolysiloxane hybrid powder of the present invention is characterized that a silicon atom of organopolysiloxane is bonded by covalent bond with a metal atom through an oxygen atom. By covalent bond in this state, a hybrid in which metal oxide and organopolysiloxane are forming uniform hybrid can be obtained. Desirably, the organopolysiloxane is the compound which forms residue group represented by general formula (1),

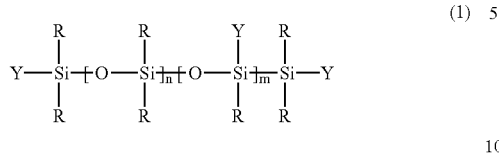 (1)

Wherein, R is an alkyl group, an aryl group or an aralkyl group and can be same or can be different, Y is a group represented by —R or —R$^1$—Si(—O—)$_3$, wherein R$^1$ is an alkylene group of carbon number 1-5, and can be same or can be different and at least one is —R$^1$—Si(—O—)$_3$, n=1-100 and m=0-5.

As a metal of metal oxide which forms hybrid with organopolysiloxane, titanium, zirconium, aluminum, iron cerium, zinc, copper and yttrium can be mentioned, further silicon can be also used. These metal oxides can be used alone or can be used together with. Among the metal oxides, titanium oxide and zirconium oxide can be preferably used. As illustrated later, these metal oxide can be prepared by using alkoxide (compound prepared by substituting hydrogen atom of hydroxyl group of alcohol with metal) as a starting material, and converted to a metal oxide at the process for forming hybrid. As alkoxide used in the present invention, methoxide, ethoxide, propoxide, isopropoxide and butoxide can be mentioned.

And, as organopolysiloxane used to form hybrid with metal oxide, any kind of organopolysiloxane which has a reactive functional group at the end or at a side chain (called as reactive organopolysiloxane in the present invention) can be used, however, not intend to be limited to them. Above mentioned reactive functional group is an alkoxy group, a silanol group, a carboxyl group, an amino group or an epoxy group, and especially, organopolysiloxane possessing an alkoxy group or a silanol group (in the present invention, these mentioned organopolysiloxane possessing an alkoxy group or a silanol group are shortened simply to organopolysiloxane containing alkoxy group) are desirably used. As an alkoxide group, methoxide, ethoxide, propoxide, isopropoxide and butoxide can be mentioned.

For example, the compound represented by following general formula (2) can be mentioned.

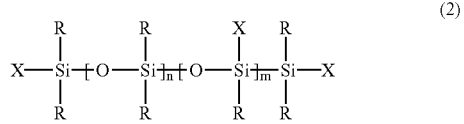 (2)

Wherein, R is an alkyl group, an aryl group or an aralkyl group and can be same or can be different, X is a group represented by —R, —H or —R$^1$—Si(OR$^2$)$_3$, wherein R$^1$ is an alkylene group of carbon number 1-5 and R$^2$ is hydrogen or an alkyl group of carbon number 1-5, can be same or can be different and at least one is —H or —R$^1$—Si(OR$^2$)$_3$, n=1-100 and m=0-5.

An alkyl group of above mentioned R is a methyl group, an ethyl group or a propyl group, and especially compound of methyl group is desirably used. And an aryl group of above mentioned R is a phenyl group or a tolyl group and an aralkyl group is a phenethyl group.

Organopolysiloxane derivatives possessing an alkoxy group represented by following general formula (3) can be desirably used,

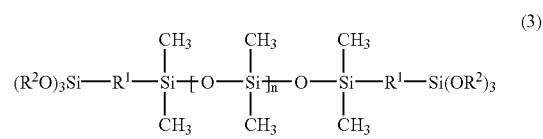 (3)

wherein R$^1$ is an alkylene group of carbon number 2-4, R$^2$ is CH$_3$ or C$_2$H$_5$ and n=6-16.

As a concrete example of those organopolysiloxane derivatives, compounds represented by following formulae (4) and (5) can be mentioned.

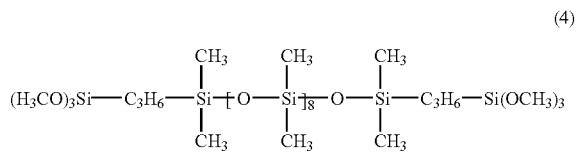 (4)

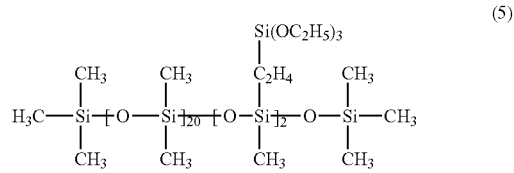 (5)

The producing method of metal oxide.organopolysiloxane hybrid powder of the present invention will be illustrated hereinafter. The metal oxide.organopolysiloxane hybrid powder of the present invention can be produced as follows. Sol is generated by hydrolysis of metal alkoxide, then reactive organopolysiloxane is added and generate hybrid sol solution. By dropping this obtained hybrid sol solution into mixed solution of alkaline aqueous solution and organic solvent, the metal oxide.organopolysiloxane hybrid powder of the present invention can be obtained. That is, so called two steps method is used, namely, at the first step, hybrid sol is synthesized and then, porous material practically using the obtained hybrid sol is obtained at the second step.

A case in which alkoxide of titanium is used as the alkoxide of metal and organopolysiloxane containing alkoxy group is used as the reactive organopolysiloxane will be illustrated. To alkoxide of titanium, the mixture of organic solvent and water is dropped and cause hydrolysis so as to generate sol. At this time, for the purpose to obtain transparent sol, it is desirable to drop the mixture solution slowly. Organopolysiloxane derivative containing alkoxy group is added to obtained sol and generate hybrid sol solution. Then the obtained hybrid sol solution is dropped into the mixed solution of alkaline aqueous solution and organic solvent, and thus titanium oxide.organopolysiloxane hybrid powder is produced. Also zirconium oxide.organopolysiloxane hybrid powder can be produced by the similar method. Further, for example, mixture of titanium oxide and zirconium oxide.organopolysiloxane hybrid powder can be produced by the similar method.

The reaction schema at the above mentioned production method of titanium oxide.organopolysiloxane hybrid powder, is theoretically explained as follows. That is hydrolysis products of titanium oxide and organopolysiloxane derivative are polycondensed to each other, and forms hybrid sol. The paragraph of "titanium oxide and organopolysiloxane are homogeneously forming hybrid" in the present invention means that the separation of phase can not be observed when the powder is observed by an optical microscope. That is, it means that the titanium oxide phase and organopolysiloxane phase can not be distinguished each other by the optical microscopic observation.

Further, since the particle size of metal oxide.organopolysiloxane becomes different according to the kind of metal oxide and the producing condition, however, in general, the particle size is in the range from 1 nm to 1000 μm.

In the case when the compound represented by aforementioned general formula (3) is used as organopolysiloxane containing alkoxy group and alkoxide of titanium is used as an alkoxide of metal, the spherical titanium oxide.dimethylpolysiloxane hybrid powder can be produced by condensing alkoxide of titanium and alkoxide group containing dimethylpolysiloxane derivative by particular molar ratio, namely 1:1–10:1 molar ratio. And when condensed by molar ratio of 3:1–50:1, porous type titanium oxide.dimethylpolysiloxane hybrid powder can be produced.

Further, when the molar ratio of alkoxide of titanium and alkoxide group containing dimethylpolysiloxane derivative is settled to 3:1–10:1, spherical and porous type titanium oxide.dimethylpolysiloxane hybrid powder can be produced. And titanium oxide.organopolysiloxane hybrid powder obtained by condensing by 7:1–50:1 molar ratio can protect skin from the affect of ultra violet ray, and by adsorbing action of said hybrid powder can remove an obstacle product on the surface of skin secreted from a living body, for example, porphyrin (this compound is known to generate singlet oxygen by photo-sensitizing reaction under ultra violet ray irradiation) discharged from skin by P. acnes, which is main bacillus of skin, therefore the oxidation of skin by ultra violet ray is defended and the skin can be protected effectively.

The titanium oxide.dimethylpolysiloxane hybrid powder of the present invention superior to the conventional titanium oxide from the view point of dispersion ability, dispersing stability and water repellency, and it is possible to control refractive index and feeling of hardness which were difficult to control. And above mentioned porous type titanium oxide.organopolysiloxane hybrid powder differs from the conventional porous type silica from the view point that silicone is a composing component. Therefore, said hybrid powder has a good affinity with oil and has excellent dispersion ability and dispersing stability, further has a soft feeling. Further, since it is possible to obtain good screening effect against ultra violet ray, it can be effectively used as a powder component of cosmetic composition and a penetrating material. Still further, since said hybrid powder can adsorb hydrophobic materials such as peroxide sebum or free fatty acid existing on the surface of skin which affects skin badly, it is useful as a power material from the view point to maintain the health of skin.

The producing method of titanium oxide.dimethylpolysiloxane hybrid powder of the present invention will be illustrated more readily.

The first process: Synthesis of titanium oxide.dimethylpolysiloxane hybrid sol

Titanium tetraisopropoxide (product of Wako Junyaku Co., Ltd.) is poured into a conical flask made of polymethylpentene and stirred using a magnetic stirrer, then the mixed solution consisted of water, hydrochloric acid and organic solvent is dropped in the flask by 1.0 mL/minute and obtain transparent sol solution. Just after the dropping, the mixture consisted of alkoxy containing dimethylpolysiloxane and organic solvent is added maintaining constant stirring. Thus the titanium oxide.dimethylpolysiloxane hybrid sol of the present invention, can be obtained. The organic solvent used in the present invention, any kinds of solvent which can dissolve titanium tetraisopropoxide and alkoxy group containing organopolysiloxane can be used, however among these, 2-propanol can be preferably used.

The second process: Synthesis of titanium oxide.dimethylpolysiloxane hybrid powder Titanium oxide.dimethylpolysiloxane hybrid sol obtained by the first process is dropped into the mixed solution of ammonia, water and organic solvent and precipitated. During the dropping procedure, constant stirring is continued and after dropping the constant stirring is continued for another 30 minutes. Then, the top is separated by a centrifuge and removed, and powder part is dispersed into organic solvent again using an ultrasonic wave. Separated from the organic solvent using a centrifuge, the powder part is dried up in the room temperature or by heating, then pulverized. Thus the hybrid powder can be obtained. Any kind of organic solvent which can mix with ammonia and water can be used, however, methanol can be preferably used.

The producing method of spherical titanium oxide.dimethylpolysiloxane hybrid powder will be illustrated as follows. That is, in the synthesis of titanium oxide.dimethylpolysiloxane hybrid sol described in above mentioned first process, use organopolysiloxane represented by afore mentioned formula (4) as alkoxy group containing dimethylpolysiloxane, and synthesis hybrid sol by same process by setting up molar ratio of it to titanium tetraisopropoxide 1:1–10:1. The obtained hybrid sol is dropped into mixture of ammonia, water and methanol or ethanol, and spherical titanium oxide.dimethylpolysiloxane hybrid powder can be obtained. In this case, the spherical hybrid powder of more uniform shape can be obtained by adding lower HLB organopolysiloxane type surface-active agent to the mixture of ammonia, water and methanol. As the concrete example of the lower HLB organopolysiloxane type surface-active agent, KF-6016 (product of Shinetsu Chemical Co., Ltd.) can be mentioned.

The porous titanium oxide.dimethylpolysiloxane hybrid powder can be obtained by synthesizing hybrid sol according to same method mentioned above, by setting up molar ratio of organopolysiloxane represented by afore mentioned formula (4) to titanium tetraisopropoxide 3:1–50:1.

By heat treatment of said porous titanium oxide.dimethylpolysiloxane hybrid powder, the porous titanium oxide.silica composite can be obtained. The heating temperature is 300–700° C., desirably is 400–600° C. It is considered, that by the heating, the functional group containing carbon of organosiloxane is decomposed and forms silica. This can be confirmed by observing that the absorption band originated to e.g. Si—$CH_3$ group is vanished according to the measuring results of IR spectrum. As the result, the composite characterizing fine particles of titanium oxide is dispersing by good dispersion state in matrix of silica can be obtained, maintaining porous state.

When the temperature for said heat treatment is higher than 700° C., the structure of titanium oxide changes to anataze type crystalline and the structure becomes non-porous. Therefore, the heat treatment temperature is lower than 700° C., desirably is lower than 600° C. In the meanwhile, when the heat treatment temperature is lower than 300° C., the decomposition of organopolysiloxane is not perfect and partially becomes state of silica, therefore, in this case, the powder which has an intermediate property between porous titanium oxide.organopolysiloxane hybrid powder and porous titanium oxide.silica composite can be obtained. For the purpose to obtain the porous titanium oxide-silica composite by decomposing organopolysiloxane completely, the heat treatment temperature higher than 300° C., desirably higher than 400° C. is needed.

In the obtained porous titanium oxide.silica composite, although titanium oxide is complicated by high concentration, titanium oxide exists by fine and good dispersing state, and is quite novel from the view point of high porosity and large specific surface area. Further, silicone is converted to silica by the heat treatment, and the hydrophilic property and mechanical strength is also improved. Since this porous titanium oxide silica composite has excellent hydrophilic property, high ultra violet ray absorbing ability, high transparency and can form natural cosmetic film, said composite is suitable as the material for a cosmetic composition. Furthermore, based on it's porous property, it is expected to be used not only for cosmetic composition but also for the application as a carrier of catalyst.

The cosmetic composition of the present invention will be illustrated readily as follows. The cosmetic composition of the present invention is characterized to have good feeling at the actual use, natural makeup, long-lasting and excellent ultra violet lay screening effect by blending above mentioned hybrid powder. As the concrete example of a formulation type of cosmetic composition, a skin care cosmetic composition such as milky lotion, a make up cosmetic composition such as foundation or lipstick, a sun-screening cosmetic composition and a hair care cosmetic composition can be mentioned. The blending amount of the hybrid powder is not restricted, however, desirable blending amount is 0.1–70% by weight.

Further, to the cosmetic composition of the present invention, compounds which are used to the ordinary cosmetic composition can be added for the purpose to maintain the shape of each formation type or in accordance to various object, in the limit not to hurt the effect of the present invention. For example, emolient feeling can be provided by adding lipophilic materials including liquid and solid materials such as hydrocarbon, high fatty acid ester, oil and fat of animal or vegetable, organopolysiloxane oil or fluorine type oil. Coloring effect and powdery feeling can be provided by adding powder such as organic pigment or inorganic pigment. And moisture feeling can be provided by adding water soluble high polymer, alcohol and water. Further, a film forming agent such as surface active agent or polymer emulsion, an ultra violet ray absorbing agent, a moisture keeping agent, an anti-oxidation agent, botanicals, vitamins, humectants and a perfume can be voluntarily added to the cosmetic compound for the purpose to provide various good effects to the cosmetic composition.

EXAMPLES

The present invention will be understood more readily with reference to the Example and the Comparative Examples, however, these are only intended to illustrate the invention and not be construed to limit the scope of the invention.

Example 1

Producing Example of Titanium Oxide.dimethylpolysiloxane Hybrid Powder 50 mmol of titanium tetraisopropoxide (product of Wako Junyaku) is poured into a conical flask made of polymethylpentene and stirred using magnetic stirrer, then mixed solution of 50 mmol of water, 3 mmol of hydrochloric acid and 2-propanol is dropped into said conical flask by 1.0 mL/minute rate. Immediately after dropping, 10 mmol dimethylpolysiloxane having alkoxy group of formula (5) at side chain and 2-propanol are added by constant stirring and titanium oxide.dimethylpolysiloxane hybrid sol is obtained.

Above mentioned titanium oxide.dimethylpolysiloxane hybrid sol is dropped into the mixed solution of ammonia, water and 2-propanol and hybrid powder is synthesized. During the dropping procedure, constant stirring is continued and after dropping the constant stirring is further continued another 30 minutes. Then, the top is separated by a centrifuge and removed, and powder part is dispersed into organic solvent again using an ultrasonic wave. Separated from the organic solvent using a centrifuge, the powder part is dried up in the room temperature or by heating, then pulverized. Thus the amorphous hybrid powder is obtained.

The refractive index of the obtained titanium oxide.dimethylpolysiloxane hybrid powder is 1.54, and the dispersion ability and dispersing stability of the obtained hybrid powder are good.

Example 2

Producing Example of Spherical Titanium Oxide.dimethylpolysiloxane Hybrid Powder The same process to Example 1 except using 20 mmol of dimethylpolysiloxane of formula (4) instead of 10 mmol of dimethylpolysiloxane of formula (5) is carried out. The spherical titanium oxide.dimethylpolysiloxane hybrid powder of 1.50 refractive index having good dispersion ability and dispersing stability is obtained.

Example 3

Producing Example of Zirconium Oxide.dimethylpolysiloxane Hybrid Powder 22.57 g of 85% zirconium (IV) butoxide 1-butanol solution (50 mmol when converted into zirconium butoxide) is poured into a conical flask made of polymethylpentene and stirred using a magnetic stirrer, then 10 mmol dimethylpolysiloxane having alkoxy group and 2-propanol are added maintaining constant stirring, and zirconium oxide.dimethylpolysiloxane hybrid sol is obtained.

The hybrid powder is synthesized by dropping above mentioned zirconium oxide.dimethylpolysiloxane hybrid sol into mixed solution of ammonia, water and methanol. During the dropping procedure, constant stirring is continued and after dropping the constant stirring is further continued another 30 minutes. Then, the top is separated by a centrifuge and removed, and powder part is dispersed into organic solvent again using an ultrasonic wave. Separated from the organic solvent using a centrifuge, the powder part is dried up in the room temperature or by heating, then pulverized. Thus the amorphous hybrid powder is obtained.

The refractive index of the obtained zirconium oxide.dimethylpolysiloxane hybrid powder is 1.52, and the dispersion ability and dispersing stability of the obtained hybrid powder are good.

Example 4

Producing Example of Aluminum Oxide.dimethylpolysiloxane Hybrid Powder

By the same process to Example 3 except using 85% aluminum triisopropoxide 2-propanol solution instead of 85% zirconium (IV) butoxide 1-butanol solution and compound of general formula (2), wherein X=$C_3H_6$—Si—$(OC_2H_5)_3$, m=0, n=20 and R=$CH_3$, instead of alkoxy group containing dimethylpolysiloxane of formula (4), aluminum oxide.dimethylpolysiloxane hybrid powder is obtained

Example 5

Producing Example of Iron Oxide.dimethylpolysiloxane Hybrid Powder

By the same process to Example 3 except using 85% iron tri-n-butoxide 1-butanol solution instead of 85% zirconium (IV) butoxyde 1-butanol solution and compound of general formula (2), wherein X=$C_3H_6$—Si—$(OCH_3)_3$, m=0, n=8 and R=$CH_3$—$C_6H_5$, instead of alkoxy group containing dimethylpolysiloxane of formula (4), aluminum oxide.dimethylpolysiloxane hybrid powder is obtained

Example 6

Producing Example of Porous Titanium Oxide.dimethylpolysiloxane Hybrid Powder 100 mmol of titanium oxide of titaniumtetraisopropoxide (product of Wako Junyaku) is poured into a conical flask and stirred using a magnetic stirrer, then mixed solution of 100 mmol of water, 6 mmol hydrochloric acid and 2-propanol is dropped by 1.0 mL/minute rate. Transparent sol solution is obtained. Immediately after dropping, 5 mmol of dimethylpolysiloxane having alkoxy group of formula (4) and 2-propanol are added with constant stirring and titanium oxide.dimethylpolysiloxane hybrid sol is obtained.

The porous hybrid powder is synthesized by dropping above mentioned titanium oxide.dimethylpolysiloxane hybrid sol into mixed solution of ammonia, water and methanol. Then, the top is separated by a centrifuge and removed, and powder part is dispersed into organic solvent again using an ultrasonic wave. Separated from the organic solvent using a centrifuge, the powder part is dried up in the room temperature or by heating, then pulverized. Thus the porous titanium oxide.dimethylpolysiloxane hybrid powder is obtained.

BET specific surface area of the obtained porous titanium oxide.dimethylpolysiloxane hybrid powder is approximately 100 $m^2$/g.

Example 7

Producing Example of Porous Titanium Oxide.silica Composite

Porous titanium oxide.silica hybrid is obtained by heat treatment of porous titanium oxide.dimethylpolysiloxane hybrid powder obtained by Example 6 at 500° C. for 2 hours. BET specific surface area of this hybrid is approximately 100 $m^2$/g and pore size is approximately 1 nm.

Example 8

Producing Example of Spherical and Porous Titanium Oxide.organopolysiloxane Hybrid Powder 100 mmol of titanium oxide of titaniumtetraisopropoxide (product of Wako Junyaku) is poured into a conical flask and stirred using a magnetic stirrer, then mixed solution of 100 mmol of water, 6 mmol of hydrochloric acid and 2-propanol is dropped by 1.0 mL/minute rate. Transparent sol solution is obtained. Immediately after dropping, 20 mmol of dimethylpolysiloxane having alkoxy group of formula (4) and 2-propanol are added with constant stirring and titanium oxide.dimethylpolysiloxane hybrid sol is obtained.

The porous hybrid powder is synthesized by dropping above mentioned titanium oxide.dimethylpolysiloxane hybrid sol into mixed solution of ammonia, water and methanol. Then, the top is separated by a centrifuge and removed, and powder part is dispersed into organic solvent again using an ultrasonic wave. Separated from the organic solvent using a centrifuge, the powder part is dried up in the room temperature or by heating, then pulverized. Thus the spherical and porous titanium oxide.dimethylpolysiloxane hybrid powder is obtained.

BET specific surface area of the obtained spherical and porous titanium oxide.dimethylpolysiloxane hybrid powder is approximately 180 $m^2$/g.

Example 9

Producing Example of Spherical and Porous Titanium Oxide.silica Composite

Spherical and porous titanium oxide.silica hybrid is obtained by heat treatment of porous titanium oxide.dimethylpolysiloxane hybrid powder obtained by Example 8 at 500° C. for 2 hours. BET specific surface area of this hybrid is approximately 180 $m^2$/g and pore size is approximately 1 nm.

Example 10

Producing Example of Spherical and Porous Titanium Oxide.organopolysiloxane Hybrid Powder Spherical and porous titanium oxide.organopolysiloxane hybrid powder is obtained by same method to Example 8 except changing the amount of alkoxy group containing dimethylpolysiloxane of formula (4) to 10 mmol.

BET specific surface area of the spherical and porous titanium oxide.dimethylpolysiloxane hybrid powder is approximately 200 $m^2$/g.

Example 11

| Producing Example of oily solid sun-screening foundation | | |
|---|---|---|
| (components) | | (%) |
| 1. | hybrid powder of Example 6 | 20.0 |
| 2. | hybrid powder of Example 1 | 5.0 |
| 3. | titanium oxide (fine particle) | 10.0 |
| 4. | mica | 10.7 |
| 5. | talc | 12.0 |
| 6. | red iron oxide | 0.4 |
| 7. | yellow iron oxide | 1.8 |
| 8. | black iron oxide | 0.1 |
| 9. | ethylene propylene copolymer | 4.0 |
| 10. | carnauba wax | 6.0 |
| 11. | rhodinic acid pentaerythritol | 6.0 |
| 12. | cetyl isooctanate | 12.0 |
| 13. | propylene glycol dicaprate | 8.0 |
| 14. | liquid paraffin | 4.0 |

Producing Method

A: components 9–14 are fused by heat at 110° C.
B: components 1–8 are added to A, mixed and dispersed
C: B is heated to 80° C. and plugged into a dish from a hole made in the bottom of the dish by pressure fusing, then an oily solid sun-screening foundation is obtained.

The obtained oily solid sun-screening foundation of the present invention is excellent in the feeling at the actual use, natural makeup and long lasting, further good at the filling and molding ability. Furthermore is superior at the ultra violet ray screening effect, protects skin from oxidation and is good at the protective effect of skin. In the meanwhile, 5% treated titanium oxide by dimethylpolysiloxane (titanium oxide whose surface is treated by dimethylpolysiloxane so as the adhered amount to be 5%) is used instead of hybrid powder of Example 6 and Example 1 and comparative foundations are obtained. The foundation of the present invention is superior to said comparative foundations especially from the view points in the feeling of the actual use, natural makeup and the protective effect of skin.

Example 12

Producing Example of cosmetic lotion

| (components) | (%) |
| --- | --- |
| 1. composite of Example 7 | 8.0 |
| 2. polymethylmethacrylate | 2.0 |
| 3. 1,3-butylene glycol | 10.0 |
| 4. carboxyvinyl polymer | 0.2 |
| 5. aqueous solution of sodium hydroxide (1%) | 4.0 |
| 6. preservative | q.s. |
| 7. purified water | balance |

Producing Method

A: components 3–5 and 7 are mixed homogeneously.
B: component 6 is added to A and mixed, then components 1, 2 are added, dispersed homogeneously and mixed, thus cosmetic lotion is obtained.

The obtained cosmetic lotion of the present invention is excellent at the skin control effect, less stimulus to skin, having good sensual feature e.g. smooth feeling and not sticky and is excellent at ultra violet ray screening effect. On the contrary, pigment type titanium oxide and porous silica are used by 6:4 ratio instead of the composite of Example 7 and a comparative cosmetic lotion is obtained. The cosmetic lotion of the present invention is superior to said comparative cosmetic lotion from the view points of skin control effect and stimulus to skin.

Example 13

Producing Example of an anti-perspirant spray

| (components) | (%) |
| --- | --- |
| 1. chlorohydroxyaluminum | 3.0 |
| 2. isopropylmyristate | 1.0 |
| 3. glyceryl tri(2-ethylhexanoate) | 2.0 |
| 4. hybrid powder of Example 8 | 1.0 |
| 5. ethanol | 2.9 |
| 6. polyoxyethylenealkyletherphosphate | 0.1 |
| 7. liquid petroleum gas | 90.0 |

Producing Method

A: components 1 and 4 are mixed, then components 2, 3, 5 and 6 are added and mixed.
B: A is contained into an air sol container and component 7 is added.

Thus the antiperspirant spray of the present invention is obtained. The original liquid of the obtained anti-perspirant spray is homogeneous and stable slurry. And has good smooth feeling when sprayed and coated to skin. Further, white residue by powder is not observed. And, oxidation of skin can be effectively prevented.

Example 14

Producing Example of shampoo

| (components) | (%) |
| --- | --- |
| 1. sodium N-lauroyl-L-glutamate | 10.0 |
| 2. coconut oil fatty acid-L-potassiumglutamate | 15.0 |
| 3. coconut oil fatty acid monoethanolamide | 2.0 |
| 4. cationated gua gum | 0.5 |
| 5. composite of Example 9 | 1.0 |
| 6. perfume | q.s. |
| 7. preservative | q.s. |
| 8. purified water | balance |

Producing Method

A: Components 1–4, 7 and 8 are heated and fused homogeneously and mixed.
B: Component 5 is added to A and mixed homogeneously.
C: B is cooled down to 40° C., add component 6 and mixed homogeneously.
D: C is defoamed and shampoo is obtained.

The obtained shampoo of the present invention is very gentle to skin and hair, contamination on scalp and pores are effectively removed and has good feeling. There is no creak at rinsing, and powder is dispersed homogeneously.

Example 15

Producing Example of milky lotion

| (components) | (%) |
| --- | --- |
| 1. decamethylcyclopentasiloxane | 15.0 |
| 2. polyoxyethylenesorbitanemonostearate (20 E.O.) | 0.5 |
| 3. sucrose fatty acid ester | 0.5 |
| 4. 1,3-butyleneglycol | 15.0 |
| 5. carboxyvinyl polymer | 0.3 |
| 6. sodium hydroxide | 0.1 |
| 7. hybrid powder of Example 10 | 20.0 |
| 8. purified water | balance |

Producing Method

Components 1 to 3 are heated and fused homogeneously, then components 4 to 8, which are previously heated and mixed, are added and stirred so as to be emulsified and cooled down to the room temperature. Thus the milky lotion of the present invention is obtained.

The obtained milky lotion of the present invention has not only excellent skin fat controlling effect, but also has good and lightly extending feature, has good intimacy to skin and even after intimated do not become dry and rough and has smooth feeling. Further, the obtained milky lotion has an excellent ultra violet ray screening effect and protect skin from oxidation effectively. Namely, the obtained milky lotion has an excellent skin protection effect. On the contrary, 5% treated titanium oxide by dimethylpolysiloxane is used instead of hybrid powder of Example 10 and a comparative milky lotion is obtained. The milky lotion of the present invention is superior to said comparative milky lotion from the view point of skin fat controlling effect, extending feature, feeling at the actual use and skin protection effect.

Example 16

Producing Example of powder foundation

| (components) | (%) |
| --- | --- |
| 1. hybrid powder of Example 10 | 30 |
| 2. talk | 20 |
| 3. mica | balance |
| 4. colored pigment (red iron oxide, yellow iron oxide, black iron oxide) | q.s. |
| 5. vaseline | 1 |
| 6. liquid paraffin | 2 |
| 7. dimethylpolysiloxane | 3 |
| 8. perfume | q.s. |

Producing Method

To the mixture prepared by mixing components 1 to 4, components 5 to 8, which are previously heated, fused and mixed, are added and dispersed and molded by pressing.

The obtained powder foundation of the present invention is excellent in the feeling at the actual use, natural makeup and long lasting effect. Further, the obtained powder foundation has an excellent ultra violet ray screening effect and protect skin from oxidation effectively. Namely, the obtained powder foundation has an excellent skin protection effect. On the contrary, 5% treated titanium oxide by dimethylpolysiloxane is used instead of hybrid powder of Example 10 and the comparative powder foundation is obtained. The powder foundation of the present invention is superior to said comparative powder foundation from the view point of the feeling at the actual use, natural makeup and skin protection effect.

Example 17

Producing Example of W/O type emulsified foundation

| (components) | (%) |
| --- | --- |
| 1. polyoxyethylene · methylpolysiloxane copolymer | 2.0 |
| 2. octamethylcyclotetrasiloxane | 10.0 |
| 3. glyceryl tri(2-ethylhexanoate) | 5.0 |
| 4. liquid paraffin | 3.0 |
| 5. sorbitan sesquioleate | 1.0 |
| 6. hybrid powder of Example 10 | 15.0 |
| 7. red iron oxide | 0.2 |
| 8. yellow iron oxide | 1.5 |
| 9. black iron oxide | 0.2 |
| 10. glycerin | 5.0 |
| 11. 1,3-butyleneglycol | 5.0 |
| 12. purified water | q.s. |
| 13. organic modified bentonite | 0.5 |
| 14. liquid paraffin | 10 |
| 15. perfume | q.s. |

Producing Method

Components 1 to 5 are mixed together, then previously mixed components 6 to 9 are added and mixed, and components 10 to 12 are further added and emulsified. Components 13 to 15 are added to the emulsion. Thus the W/O type emulsified foundation is obtained.

The W/O type emulsified foundation of the present invention is excellent in the feeling of the actual use, natural makeup and long lasting, and has an excellent ultra violet ray screening effect. 5% treated titanium oxide by dimethylpolysiloxane is used instead of hybrid powder of Example 10 and a comparative foundation is obtained. The W/O type emulsified foundation of the present invention is superior to said comparative foundation from the view point of the feeling at the actual use and natural makeup.

Example 18

Producing Example of double layer type foundation

| (components) | (%) |
| --- | --- |
| 1. polyoxyethylene · methylpolysiloxane copolymer | 2.0 |
| 2. octamethylcyclotetrasiloxane | 10.0 |
| 3. glyceryl tri(2-ethylhexanoate) | 5.0 |
| 4. liquid paraffin | 3.0 |
| 5. sorbitan sesquioleate | 0.1 |
| 6. polyoxyethylenesorbitan trioleate (20 E.O.) | 0.1 |
| 7. ethanol | 10.0 |
| 8. glycerin | 5.0 |
| 9. 1,3-butyleneglycol | 5.0 |
| 10. purified water | balance |
| 11. hybrid powder of Example 6 | 15.0 |
| 12. red iron oxide | 0.2 |
| 13. yellow iron oxide | 1.5 |
| 14. black iron oxide | 0.2 |
| 15. perfume | q.s. |

Producing Method

Components 1 to 6 are mixed together, then previously mixed components 7 to 10 are added and emulsified. Then, mixture of components 11 to 14 and component 15 are added and mixed. Thus the double layer type foundation is obtained.

The double layer type foundation of the present invention is excellent from the view point of the feeling at the actual use, natural makeup, long lasting and ultra violet ray screening effect. 5% treated titanium oxide by dimethylpolysiloxane is used instead of hybrid powder of Example 6 and the comparative double layer type foundation is obtained. The double layer type foundation of the present invention is superior to said comparative foundation from the view point of the feeling at the actual use and natural makeup.

Example 19

Producing Example of W/O type sun-screening milky lotion

| (components) | (%) |
|---|---|
| 1. dimethylpolysiloxane | 2 |
| 2. decamethylcyclopentasiloxane | 30 |
| 3. polyether modified silicone | 3 |
| 4. 2-ethylhexyl paramethoxyciannamate | 7 |
| 5. organic modified bentonite | 1 |
| 6. hybrid powder of Example 10 | 20 |
| 7. purified water | balance |
| 8. preservative | q.s. |

Producing Method

After components 1 to 6 are dispersed, components 7 and 8 are added and emulsified. Thus the W/O type sun-screening milky lotion is obtained.

The W/O type sun-screening milky lotion of the present invention is excellent from the view point of the feeling at the actual use, long-lasting, and ultra violet ray screening effect. 5% treated titanium oxide by dimethylpolysiloxane is used instead of hybrid powder of Example 10 and the comparative W/O type sun-screening milky lotion is obtained. The W/O type sun-screening milky lotion of the present invention is superior to said comparative W/O type sun-screening milky lotion from the view point of the feeling at the actual use and natural looking.

Example 20

Producing Example of O/W type sun-screening milky lotion

| | (components) | (%) |
|---|---|---|
| 1. | hybrid powder of Example 10 | 10.0 |
| 2. | 2-ethylhexyl paramethoxyciannamate | 2.0 |
| 3. | stearic acid | 2.0 |
| 4. | cetanol | 1.0 |
| 5. | vaseline | 2.0 |
| 6. | dimethylpolysiloxane | 5.0 |
| 7. | liquid paraffin | 5.0 |
| 8. | glyceryl monostearate | 1.0 |
| 9. | polyethylene glycol (23 mol) monooleate | 1.0 |
| 10. | polyethylene glycol 1500 | 5.0 |
| 11. | bee gum | 0.5 |
| 12. | triethanolamime | 1.0 |
| 13. | purified water | balance |
| 14. | perfume | q.s. |
| 15. | preservative | q.s. |

Producing Method

After components 1 to 7 are heated, mixed together and dispersed, previously mixed components 8 to 11 are added and emulsified. Then components 12 to 15 are added and mixed. Thus the O/W type sun-screening milky lotion is obtained.

The O/W type sun-screening milky lotion of this invention is excellent from the view point of the feeling at the actual use, natural looking, long-lasting and ultra violet ray screening effect. 5% treated titanium oxide by dimethylpolysiloxane is used instead of hybrid powder of Example 10 and a comparative O/W type sun-screening milky lotion is obtained. The O/W type sun-screening milky lotion of this invention is superior to said comparative milky lotion from the view point of the feeling at the actual use and natural looking.

Example 21

Producing Example of concealer

| (components) | (%) |
|---|---|
| 1. candelilla wax | 4 |
| 2. paraffin wax | 5 |
| 3. vaseline | 5 |
| 4. dimethylpolysiloxane | 10 |
| 5. squalane | 10 |
| 6. diglyceryltriisostearate | balance |
| 7. hybrid powder of Example 10 | 45 |
| 8. nylon powder | 5 |
| 9. colored pigment | q.s. |
| (red iron oxide, yellow iron oxide, black iron oxide) | |
| 10. antioxidation agent | q.s. |
| 11. perfume | q.s. |
| (producing method) | |

Producing Method

After components 1 to 6 are heated and fused, components 7 to 11 are added and mixed homogeneously, filled up into a container, then cooled and solidified. Thus the concealer of the present invention is obtained.

The concealer of the present invention is excellent from the view point of the feeling at the actual use, natural makeup, long-lasting and ultra violet ray screening effect. 5% treated titanium oxide by dimethylpolysiloxane is used instead of hybrid powder of Example 10 and a comparative concealer is obtained. The concealer of the present invention is superior to the said comparative concealer from the view point of the feeling at the actual use and natural makeup.

Example 22

Producing Example of face powder

| (components) | (%) |
|---|---|
| 1. talc | 30.0 |
| 2. composite of Example 9 | 10.0 |
| 3. hybrid powder of Example 8 | 30.0 |
| 4. mica | balance |
| 5. red iron oxide | 0.2 |
| 6. yellow iron oxide | 0.5 |
| 7. black iron oxide | 0.05 |
| 8. dimethylpolysiloxane | 2.0 |
| 9. liquid paraffin | 3.0 |
| 10. preservative | q.s. |
| 11. perfume | q.s. |
| (producing method) | |

Producing Method

After components 1 to 7 are mixed, the previously heated and fused mixture of components 8 to 10 and component 11 are added and mixed, then pulverized and molded by pressing. Thus the face powder of the present invention is obtained.

The face powder of the present invention is excellent from the view point of the feeling at the actual use, natural makeup, long lasting and ultra violet ray screening effect. Pigment type titanium oxide and porous silica are used by 4:6 ratio instead of composite of Example 9 and 5% treated zirconium oxide by dimethylpolysiloxane is used instead of hybrid powder of Example 8 and comparative face powders are obtained. The face powder of the present invention is superior to said comparative face powders from the view point of the feeling at the actual use and natural makeup.

Example 23

Producing Example of a pressed type eye shadow

| (components) | (%) |
| --- | --- |
| 1. mica | balance |
| 2. talc | 20.0 |
| 3. titanated mica | 5.0 |
| 4. boron nitrate | 5.0 |
| 5. hybrid powder of Example 2 | 3.0 |
| 6. ultramarine blue | 2.0 |
| 7. D & C yellow No. 401 | 0.5 |
| 8. squalane | 2.0 |
| 9. vaseline | 1.0 |
| 10. dimethylpolysiloxane | 3.0 |
| 11. preservative | q.s. |
| (producing method) | |

Producing Method

Components 1 to 7 are mixed together, then previously mixed mixture of components 8 to 11 is added and mixed. After that pulverized and molded by pressing, and the pressed type eye-shadow of the present invention is obtained.

The eye-shadow of the present invention is excellent from the view point of the feeling at the actual use and long-lasting. 5% treated titanium oxide by dimethylpolysiloxane is used instead of hybrid powder of Example 2 and a comparative pressed type eye-shadow is obtained. The eye-shadow of the present invention is superior to said comparative pressed type eye-shadow from the view point of the feeling at the actual use.

Example 24

Producing Example of lipstick

| (components) | (%) |
| --- | --- |
| 1. polyisobutylene | 5.0 |
| 2. ceresin wax | 10.0 |
| 3. candelilla wax | 5.0 |
| 4. carnaubawax | 3.0 |
| 5. glyceryl tri(2-ethylhexanoate) | 20.0 |

-continued

Producing Example of lipstick

| (components) | (%) |
| --- | --- |
| 6. diglyceryl triisostearate | 20.0 |
| 7. vaseline | 5.0 |
| 8. caster oil | balance |
| 9. hybrid powder of Example 2 | 3.0 |
| 10. D & C Red No. 202 | 3.0 |
| 11. D & C Yellow No. 4 aluminum lake | 1.5 |
| 12. perfume | q.s. |
| (producing method) | |

Producing Method

Components 1 to 8 are heated and fused, then the mixture of components 9 to 11 is added and kneaded by a three shafts roll mill. After heated component 12 is added and mixed, then filled up in a container. By cooling down, the lipstick of the present invention is obtained.

The lipstick of the present invention is excellent from the view point of the feeling at the actual use, long-lasting and ultra violet ray screening effect. 5% treated titanium oxide by dimethylpolysiloxane is used instead of hybrid powder of Example 2 and a comparative lipstick is obtained. The lipstick of the present invention is superior to said comparative lipstick from the view point of the feeling at the actual use.

Example 25

Producing Example of nail enamel

| (components) | (%) |
| --- | --- |
| 1. nitrocellulose | 10.0 |
| 2. alkyd resin | 10.0 |
| 3. acetyltributylcitrate | 4.0 |
| 4. dl-camphor | 1.0 |
| 5. organic modified bentonite | 1.0 |
| 6. ethylacetate | 20.0 |
| 7. butylacetate | balance |
| 8. 2-propanol | 5.0 |
| 9. D & C Red No. 202 | 0.1 |
| 10. hybrid powder of Example 2 | 0.5 |
| (producing method) | |

Producing Method

Compounds 1 to 10 are mixed.

The nail enamel of the present invention obtained as above is excellent from the view point of dispersing ability of pigment, settling ability, long lasting and luster of the coated film. When 5% treated titanium oxide by dimethylpolysiloxane is used instead of hybrid powder of Example 2 the obtained nail enamel is inferior to that of the present invention at the view point of dispersing ability of pigment, settling ability, long lasting and luster of the coated film.

Effect of the Invention

The metal oxide.organopolysiloxane of the present invention can improve various properties of metal oxide powder. That is, by hybridizing metal oxide with organopolysiloxane, optical property of metal oxide powder, e.g. refractive

The invention claimed is:

1. A method for producing a porous powder comprising metal oxide.organopolysiloxane homogeneous hybrid particles which comprises; generating sol by hydrolysis of titanium alkoxide, adding organopolysiloxane derivatives possessing end alkoxy groups represented by general formula (3) so as the molar ratio of alkoxide of titanium and said organopolysiloxane derivatives to be 3:1–50:1, to said sol to generate hybrid sol solution,

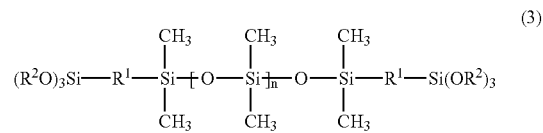

wherein $R^1$ is an alkylene group of carbon number 2-4, $R^2$ is $CH_3$ or $C_2H_5$ and n=6-16, then dropping the obtained hybrid sol solution into mixed solution of alkaline aqueous solution and organic solvent and recovering a porous powder.

2. The method for producing a porous powder of claim 1 prepared by heat treatment of porous titanium oxide.organopolysiloxane homogenous hybrid particles, wherein a silicon atom of the organopolysiloxane is bonded by covalent bond with a titanium atom through an oxygen atom and hybridized homogeneously and whose specific surface area is larger than 50 $m^2/g$.

* * * * *